United States Patent [19]
Richter et al.

[11] Patent Number: 6,065,710
[45] Date of Patent: May 23, 2000

[54] APPARATUS FOR WINDING AND UNWINDING CABLES AND DEVICE WITH SUCH AN APPARATUS

[75] Inventors: Helmut Richter, Baiersdorf; Peter Sypien, Uehfeld, both of Germany

[73] Assignee: Siemens Aktiengesellschaft, Munich, Germany

[21] Appl. No.: 09/161,667

[22] Filed: Sep. 29, 1998

[30] Foreign Application Priority Data

Sep. 30, 1997 [DE] Germany .......................... 197 43 215

[51] Int. Cl.[7] .................................................. B65H 75/38
[52] U.S. Cl. .............................. 242/388.6; 191/12.2 R
[58] Field of Search ............................... 242/386, 388.6, 242/390.8, 385.4, 396.2, 396.4; 191/12.2 R, 12.4

[56] References Cited

U.S. PATENT DOCUMENTS

| | | | |
|---|---|---|---|
| 231,033 | 8/1880 | Fritsch | 242/388.6 X |
| 1,465,281 | 8/1923 | Morrison | 242/385.4 X |
| 2,169,734 | 8/1939 | Hoppenstand | 191/12.2 R |
| 2,972,667 | 2/1961 | Ryder | 191/12.2 R |
| 3,199,804 | 8/1965 | Fontaine | 242/390.8 X |
| 4,565,333 | 1/1986 | Meneian | 242/386 |
| 5,145,390 | 9/1992 | Kaul | |
| 5,212,760 | 5/1993 | Goetz | 242/388.6 X |
| 5,489,010 | 2/1996 | Rogers | 191/12.2 R |

FOREIGN PATENT DOCUMENTS 89 09 486 U  12/1989  Germany .

*Primary Examiner*—Donald P. Walsh
*Assistant Examiner*—Emmanuel P. Marcelo
*Attorney, Agent, or Firm*—Hill & Simpson

[57] ABSTRACT

An apparatus for winding and unwinding cables has at least two rotatable drums. At least one cable can be wound onto or unwound from each of these drums. The drums are connected by a coupling linkage such that both the drums either wind or unwind the respective cables simultaneously. An arrangement cooperating with the coupling linkage effects winding of the unwound cables.

12 Claims, 6 Drawing Sheets

# APPARATUS FOR WINDING AND UNWINDING CABLES AND DEVICE WITH SUCH AN APPARATUS

BACKGROUND OF THE INVENTION

1. Field of the Invention

The present invention relates to an apparatus for winding and unwinding at least two cables, and to a device embodying such an apparatus wherein the cable connects a part of the device to electrically operated components mounted on the device, which can be displaced relative to a part of the device as the cables wind and unwind.

2. Description of the Prior Art

German PS 40 19 513, corresponding to U.S. Pat. No. 5,145,390, discloses an apparatus with a rotatable drum for winding and unwinding a cable. The drum has an outer hollow cylindrical drum surface which is rotatably mounted about an inner hollow cylindrical drum surface that is stationary relative to the outer drum surface. The outer drum surface accepts cables respectively in the form of a round cable. The ribbon cable and the round cable can be wound and unwound in opposite directions onto different regions of the outer drum surface. The apparatus is arranged in a first part of a device which has a second part with electrically operated components, the second part being displaceable relative to the first part. The ribbon cable electrically connects the two parts of the device to each other. Respective ends of the ribbon cable and the round cable are secured at opposite ends of the second part of the device. Given exertion of a tensile force on the ribbon cable by displacement of the two parts of the device relative to each other, the ribbon cable is unwound from the rotatable drum, and the round cable is wound onto the drum, and given exertion of a tensile force on the round cable by opposite displacement of the two parts of the device relative to each other, the round cable is unwound from the drum, and the ribbon cable is wound onto the drum. A spring via which the round cable end is secured at the other part of the device causes a constant tensile force to be exerted on the round cable and thus on the ribbon cable, so that this is wound onto the drum with a slight initial tension.

In order to enable the winding and unwinding of the ribbon cable at all (the ribbon cable is connected at its other end to an energy supply and to a control and signal processing unit, for example) a region of the ribbon cable is wound around the inner drum surface in a spiral surface (helix). The shell surfaces of the two hollow cylindrical drums each have an opening through which the ribbon cable is conducted. The ribbon cable is first conducted into the region between the drum surfaces through the opening of the shell surface of the inner drum via a side opening of the inner drum, is wound in spirals about the inner drum and is conducted to the outside through the opening of the shell surface of the outer drum. The region of the ribbon cable located between the drums is secured at the inner drum surface and outer drum surface with its sectional ends such that given rotation of the outer drum around the inner drum the ribbon cable is wound onto the shell surface of the outer drum, or is unwound therefrom. Given winding or unwinding of the ribbon cable onto or from the outer drum, the spiral formed by the region of the ribbon cable lying between the drums narrows in the direction of the shell surface of the inner drum, or broadens.

The known apparatus is only suitable for accepting a ribbon cable, which can be wound onto or unwound from the outer drum reliably—i.e. without loop formation. A disadvantage is that ribbon cables are expensive and have a high space requirement in winding onto a drum.

SUMMARY OF THE INVENTION

An object of the present invention is to provide an apparatus of the above-mentioned wherein simultaneous winding and unwinding of at least two cables is possible, even two round cables. It is additionally an object of the invention to provide a device embodying such an apparatus wherein the transmission of energy and signals from the part of the device to the electrically operated components is free of interference.

The first object is inventively achieved in an apparatus having at least two rotatable drums onto which at least one cable can be wound or unwound, respectively, a coupling linkage connecting the drums such that the two drums either wind or unwind the respective cable, and an arrangement cooperating with the coupling linkage which effects the winding of the unwound cables. Not only ribbon cables but also (and preferably) round cables can be wound and unwound with the inventive apparatus. The two drums can be constructed such that more than one cable can be wound onto each of the drums and unwound therefrom. If, for example, the apparatus accepts three cables, then one cable is wound or unwound on one drum, and the other two cables are wound onto different regions of the other drum, or re unwound therefrom. The winding and unwinding of the three cables ensues simultaneously, dependent on by the interaction of the two drums produced by the coupling linkage. The two drums preferably rotate around respective axes which are different and which are disposed substantially parallel to each other, whereby other drums can be connected in parallel fashion to one or both drums, these other drums performing the same rotational motions as the drums to which they are connected in parallel fashion. The coupling linkage preferably connects the two drums to each other such that the two drums move in opposite directions. The arrangement effecting the winding of the unwound cables can, for example, be an energy store for a force that serves for the winding of the cables, this force being built up when the cables are unwound from the drums with the exertion of a tensile force. With the inventive apparatus two or more cables can be simultaneously wound onto the drums of the apparatuses and unwound therefrom.

The coupling linkage can be a mechanical linkage. The coupling linkage can be a toothed gear wheel, chain entrained or belt round wheels, which are all mechanically robust and inexpensive.

In one embodiment of the invention the energy store is a tension spring and a rope which can be wound on a rotatable rope drum, the rope cooperating with the tension spring, whereby the rope drum is coupled with the coupling linkage. In this embodiment, the rope drum is coupled with the coupling linkage via either a toothed gear wheel, a chain or a belt. In the unwinding of the cables, from the drums with the exertion of a tensile force on the cables the tension spring is stressed by the rotation of the drums via the coupling linkage and the rope is simultaneously wound onto the rope drum. In the opposite direction, when there is no tensile or retention force, the relaxing of the tension spring actuates the drums so that the cables are wound onto the drums.

In a further variation of the invention the arrangement which effects the winding is a drive mechanism that cooperates with the coupling linkage or with one of the two drums. The drive mechanism is preferably an electromotor, so that the winding and unwinding of the cables can be effected in motorized fashion.

In a preferred embodiment of the invention each of the drums has an outer hollow cylindrical drum which is rotatable around an inner hollow cylindrical drum that is stationary in relation to the outer drum, whereby each cable which can be wound and unwound on an outer drum is conducted into the space between the outer and inner drum via an opening of the outer drum, and is wound about the inner drum in a spiral shape in a guide helix which is laid loosely (i.e., movably) around the inner drum. Since the diameter and the number of the turns of the cables in the space between the outer and inner drums changes in the winding and unwinding processes of the cables on the outer drums, the guide helix advantageously guarantees a uniform position of the cables in the space between the outer and inner drums for every case. Since the guide helix laid over the inner drum loosely and since its flights are movable, the flights of the helix automatically compress or expand to adjust to the number of turns of the cable. If a number of cables are wound or unwound onto different regions of a drum then, for each cable, a region that accepts the cable wound in a guide helix is provided in the space between the inner and outer drum, each region having it own guide helix. The individual regions are constructed in separated fashion.

The second object relating to a device is achieved in a device embodying an inventive apparatus as described above with cables for transmitting electrical energy and/or signals from a part of the device to electrically operated components that can be displaced with respect to the part of the device. According to one variation of the invention, cables for transmitting energy and cables for transmitting signals can be separated in the inventive apparatus for winding and unwinding at least two cables. Because of the separation of energy and signal cables, fewer disturbances arise due to crosstalk of energy onto signal cables, and thus fewer disturbances arise in the operation of the device.

The second part of the device can be fashioned as a curved part, such as a C-arm, this part being secured at a part of the device fashioned as a holder for the curved part and being displaceably mounted along its perimeter at the holder. The two cables connect the holder and the curved part to each other, with the cables being fixed at the curved part and, contained within the curved part, they are led to an x-ray source and/or to an x-ray receiver respectively mounted at opposite ends of the curved part. The containment of the cables, e.g. in a hollow interior space of the curved part, serves for protection of the cables against damage. The cables are conducted to the opposite ends of the C-arm at which the x-ray source and the x-ray receiver are respectively mounted, opposite each other. At least one cable for transmitting energy and at least one cable for transmitting signals are preferably provided. The C-arm can contain cables running from one end thereof to the other, which transmit signals from one end of the C-arm to the other.

DESCRIPTION OF THE PREFERRED EMBODIMENTS

Figure 1:
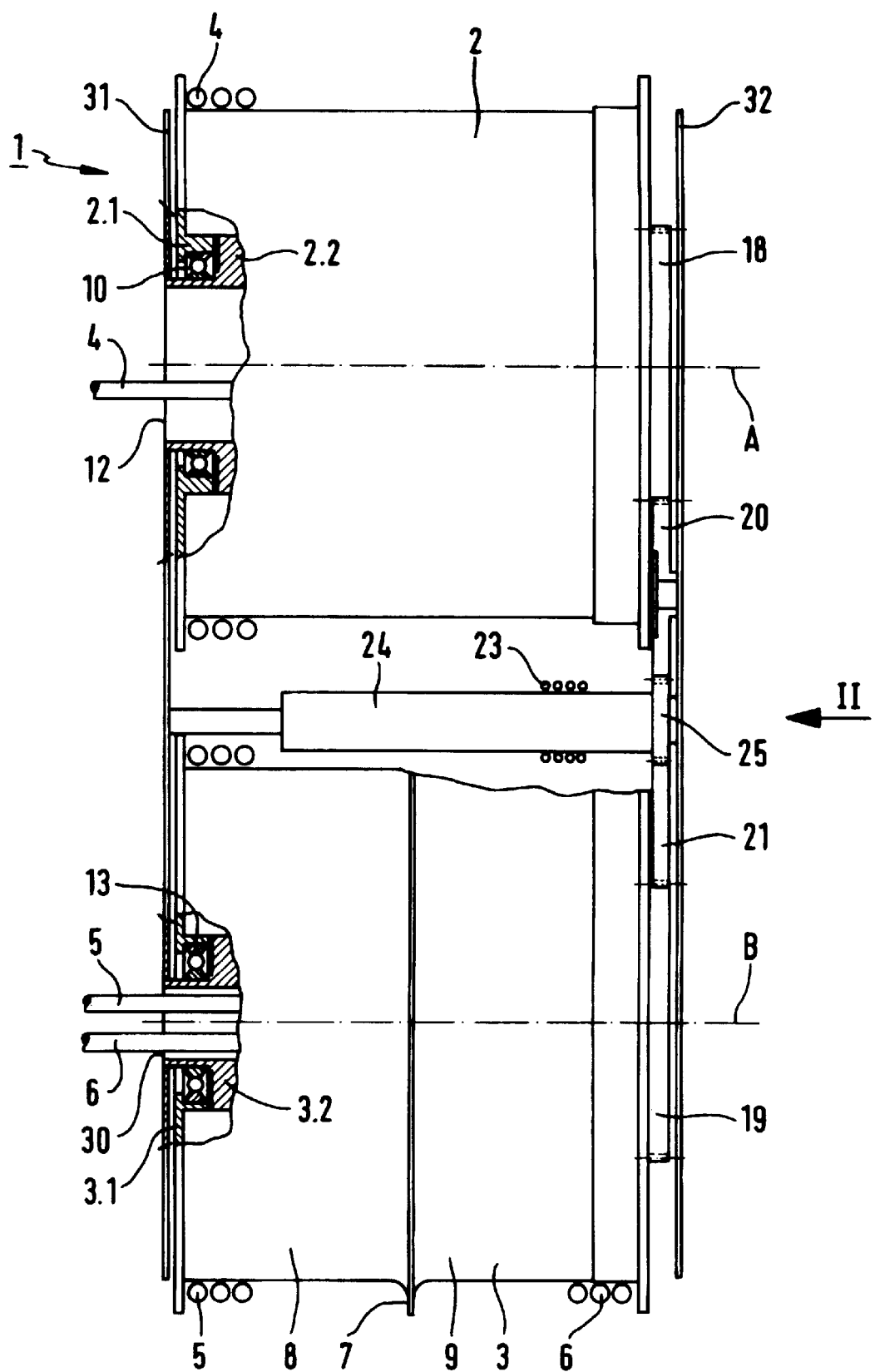
FIG. 1 shows an inventive apparatus for winding and unwinding three cables.

FIG. 1 shows an inventive apparatus 1 with two drums 2 and 3 rotatable around axes A and B, respectively. The drum 2 accepts a cable in the form of a round cable 4, and the drum 3 accepts two cables in the form of round cables 5 and 6. The drum 3 has two regions 8 and 9 for respectively accepting the cables 5 and 6, divided by a ridge 7. The cables 4 to 6 are only schematically indicated in FIG. 1.

The drum 2 has an outer hollow cylindrical drum 2.1 which is rotatable around an inner hollow cylindrical drum 2.2 that is stationary in relation to the outer drum 2.1. The outer drum 2.1 is rotatably mounted relative to the inner drum 2.2 with a ball bearing 10 and another ball bearing at the opposite side which is not visible in the figures. The cable 4 can be wound onto the outer drum 2.1 and unwound therefrom in known fashion. The cable 4 is fixed in the region of an opening of the shell surface of the outer drum 2.1 (not depicted in FIG. 1), is led through the opening into the space between the outer and inner drums 2.1, 2.2, and is wound around the inner drum 2.2 in a spiral (helical) shape in a flexible guide helix laid loosely around the inner drum 2.2 (not depicted) (cf. guide helixes 26 and 27 in FIGS. 4 and 5). The cable 4 is fixated in the region of an opening of the shell surface of the inner drum 2.2 (not depicted in FIG. 1) and is led to the outside through the opening of the inner drum 2.2 and a side opening 12 of the hollow cylindrical inner drum 2.2. During unwinding of the cable 4 from the outer drum 2.1, the cable spiral narrows in the space between the outer and inner drums 2.1, 2.2 in known fashion, while during winding the cable spiral broadens in known fashion.

Figure 2:
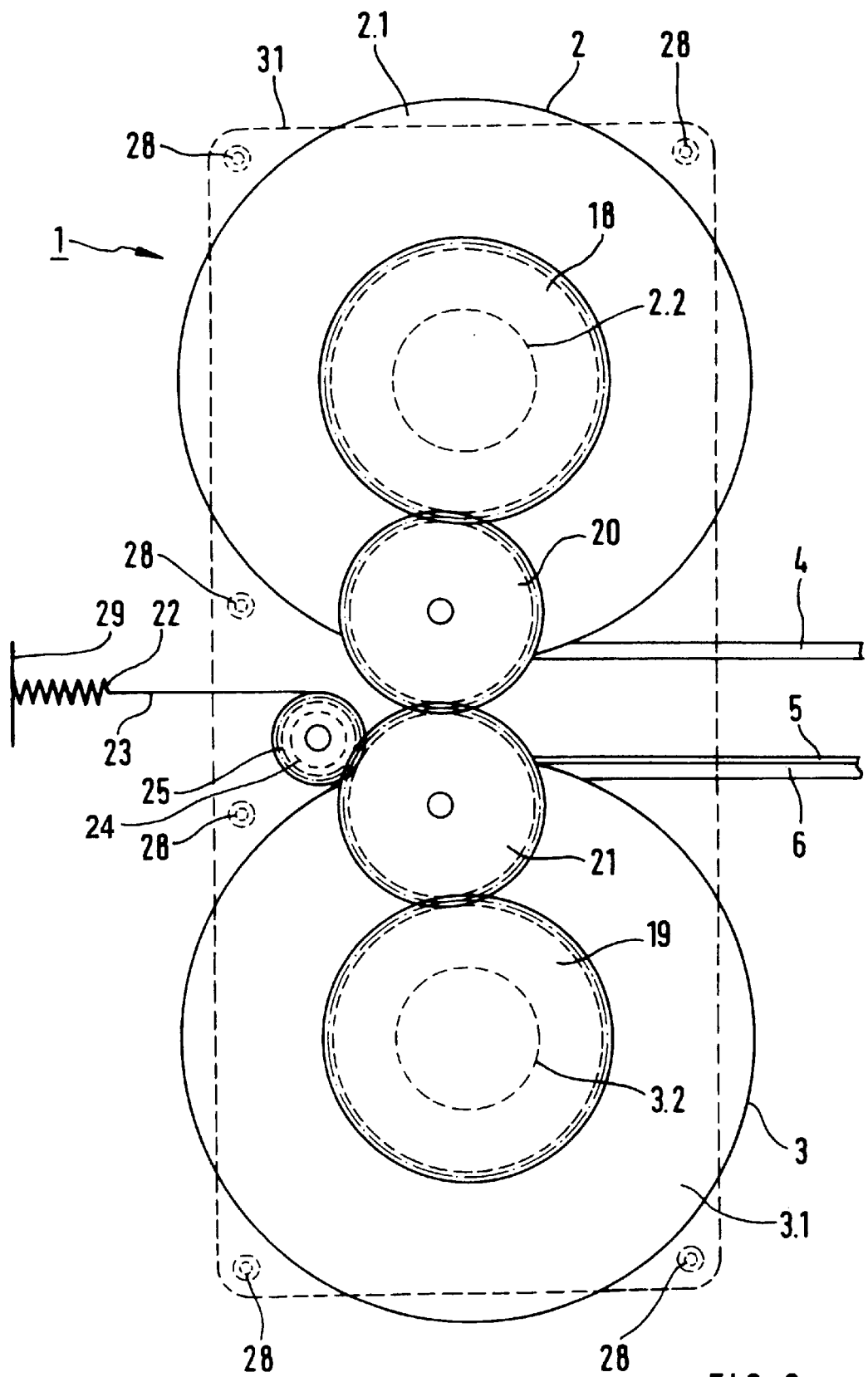
FIG. 2 is a view in the direction of the arrow II according to FIG. 1.

The drum 3 is constructed analogously to the drum 2 and has an outer drum 3.1 and an inner drum 3.2, the outer drum 3.1 being rotatably mounted relative to the inner drum 3.2 with a ball bearing 13 and another ball bearing at the opposite side which is not visible in FIGS. 1 or 2). Unlike the outer and inner drums 2.1, 2.2 of the drum 2, the outer drum 3.1 and the inner drum 3.2 of the drum 3 have respective ridges 7 and 15 separating the outer drum 3.1 into the previously mentioned regions 8, 9 and separating the inner drum 3.2 into the regions 16, 17, which are respectively provided for cables 5 and 6. The conducting of the cables 5, 6 on and in the drum 3 corresponds to the conducting of the cable 4 on and in the drum 2.

A mechanical train of toothed gear wheels which connects the two drums 2 and 3 to each other is allocated to the drums 2 and 3 as a coupling linkage. The outer drum 2.1 is securely connected to a toothed gear wheel 18 which is rotatable around the axis A together with the outer drum 2.1. The outer drum 3.1 is analogously connected securely to a toothed gear wheel 19, so that the toothed gear wheel 19 is rotatable around the axis B together with the outer drum 3.1. The toothed gear wheel 18 engages a toothed gear wheel 20; the toothed gear wheel 20 engages a toothed gear wheel 21, and the toothed gear wheel 21 engages the toothed gear wheel 19 of the train. (cf. FIG. 2), so that the outer drums 2.1 and 3.1 move in opposite directions.

The apparatus 1 is provided an arrangement formed by a tension spring 22 fixed to a stationary element 29, a rope 23, a rope drum 24 and a toothed gear wheel 25 which is securely connected to the rope drum 24 (FIGS. 1 and 2). In the exemplary embodiment the toothed gear wheel 25 engages with the toothed gear wheel 21 such that during simultaneous unwinding of the cables 4 to 6 respectively from the outer drums 2.1 and 3.1 with a tensile force exerted on one or all the cables 4 to 6, the rope 23 is wound onto the rope drum 24, thereby tensioning the tension spring 22 serving as an energy store. If a tensile force is no longer exerted on the cables 4 to 6, the tension spring 22 relaxes, causing the rope 23 to be unwound from the rope drum 24, and thereby actuating the toothed gear wheel 25 such that the outer drums 2.1 and 3.1 simultaneously wind the cables 4 to 6 via the toothed gear wheels 18 to 21 of the gear.

In addition, the drums 2, 3, the gear train, and at least a part a drive arrangement are disposed between two mounting plates 31, 32 connected to each other with screws 28 (FIG. 1).

FIG. 2 depicts a view of the apparatus 1 in the direction of the arrow II according to FIG. 1, with the mounting plate 32 removed. The mounting plate 31 is indicated with dashed lines in FIG. 2.

Figure 3:
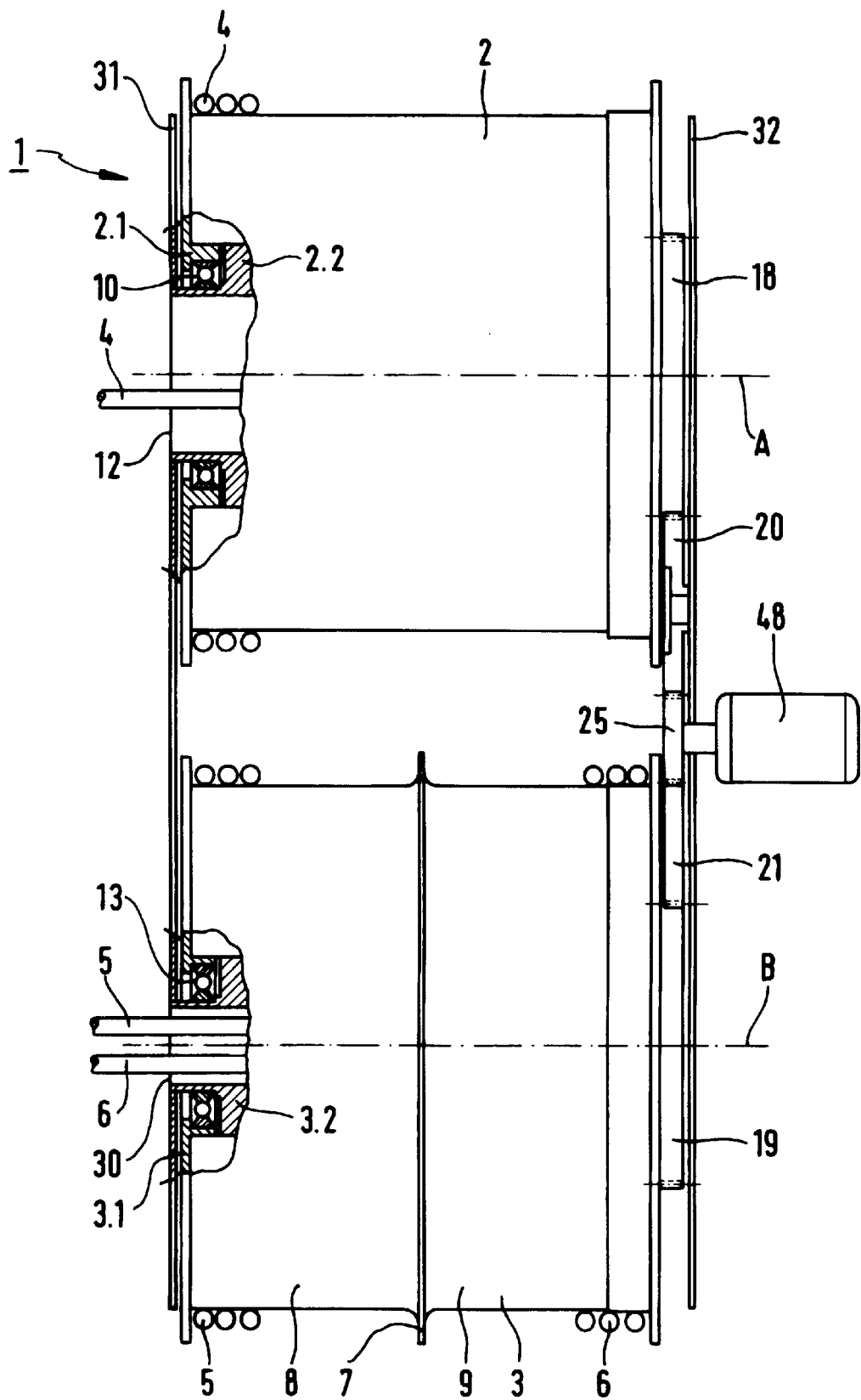
FIG. 3 shows another exemplary embodiment of an inventive apparatus.

FIG. 3 shows another embodiment of the inventive apparatus 1 wherein a drive mechanism in the form of an electromotor 48 is provided instead of the tension spring 22, the rope 23 and the rope drum 24. The electromotor 48 cooperates with the toothed gear wheel 25 according to the actuation direction of the electromotor 48 so that the drums 2 and 3 are actuated for the winding and unwinding of the cables 4 to 6 via the toothed gear wheels 18 to 21. Not only the unwinding but also the winding of the cables 4 to 6 can thus ensue in motorized fashion.

The electromotor 48 need not engage the toothed gear wheel 25, but can instead engage one of the toothed gear wheels 18 to 21, or can engage one of the two drums 2 or 3 directly.

Figure 4:
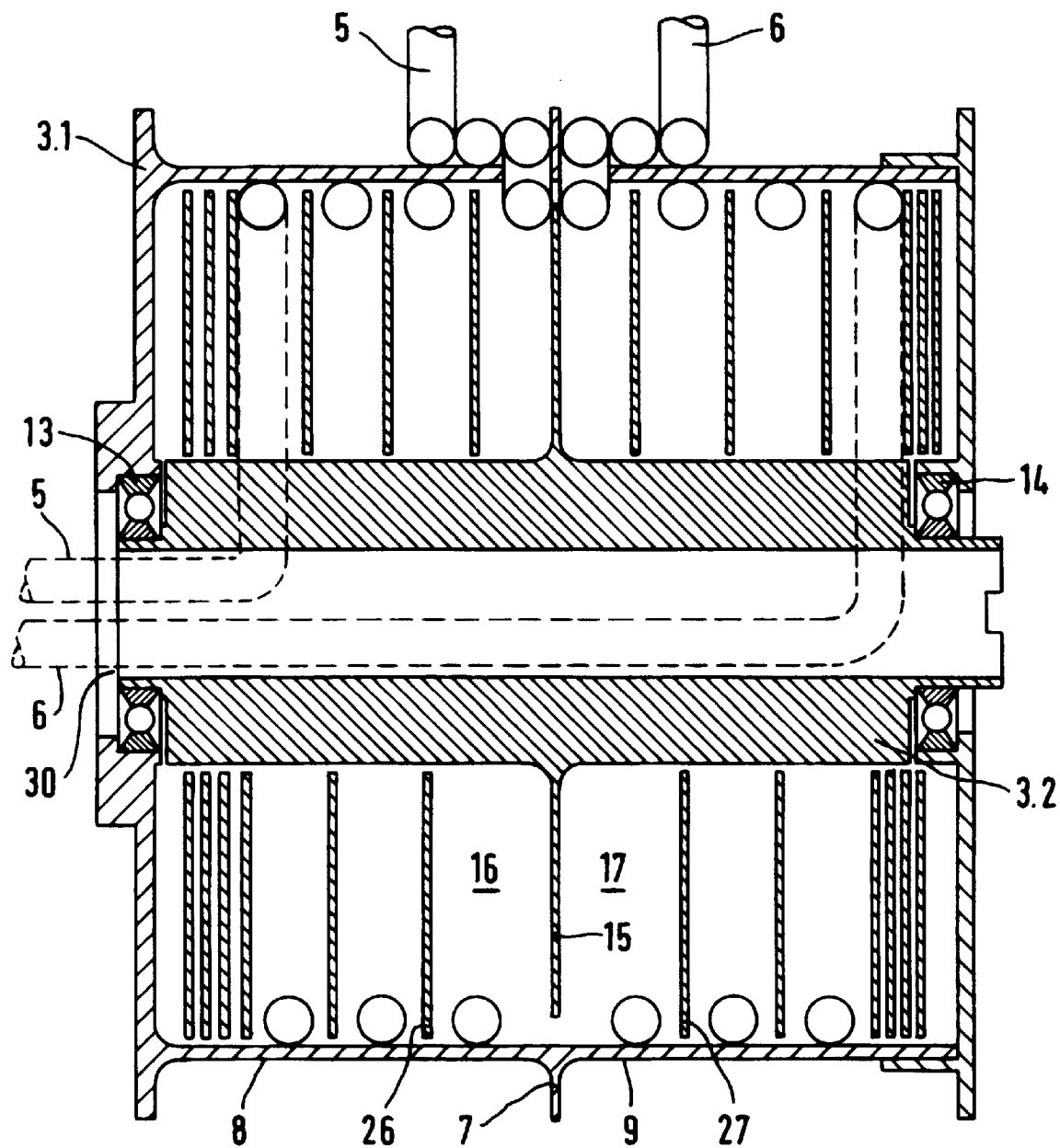
FIG. 4 is a sectional view of a drum of FIG. 1 for accepting two cables, with the cables partially wound.
Figure 5:
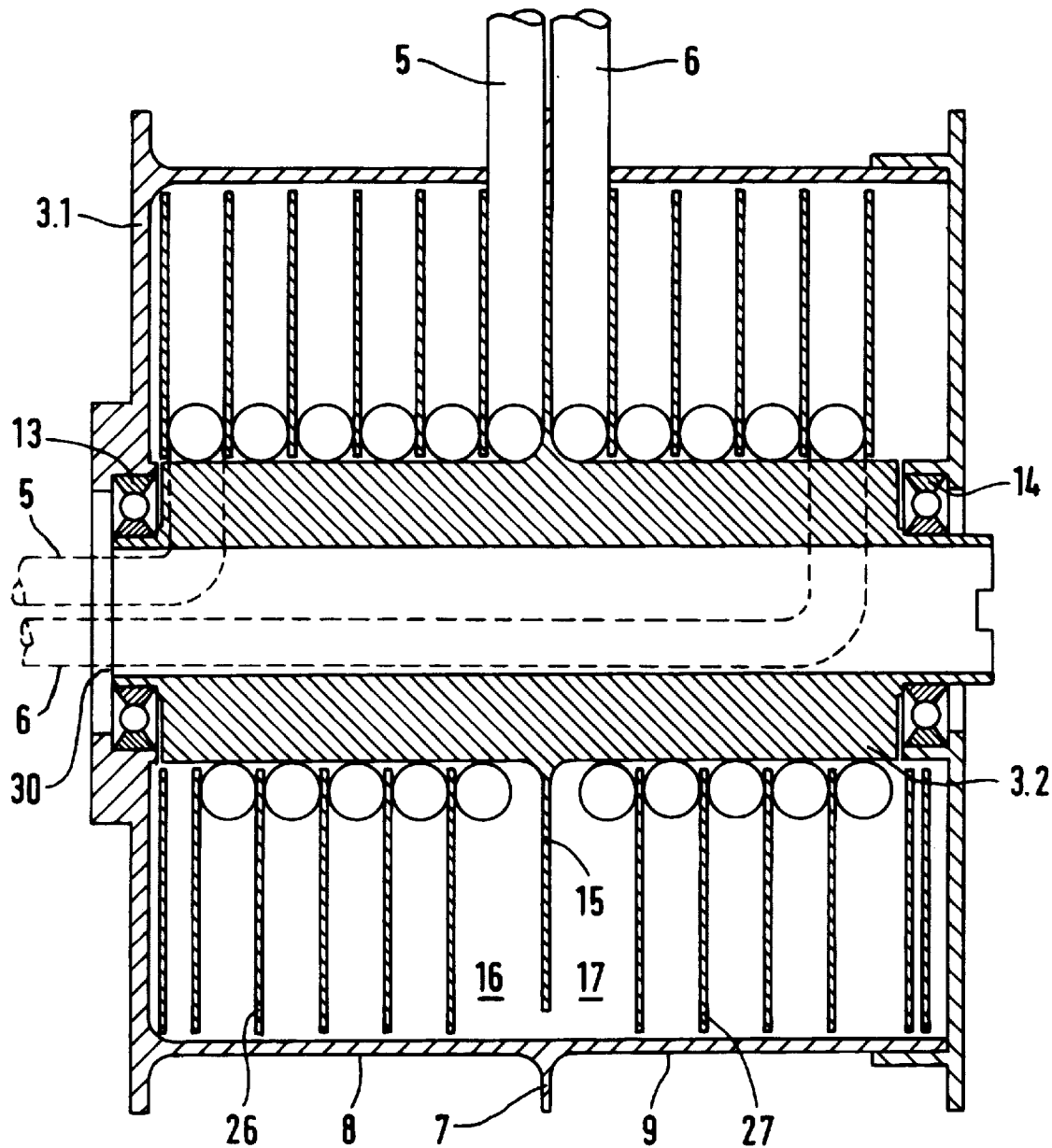
FIG. 5 is a sectional view of the drum of FIG. 4, with the cable unwound.

Using the drum 3 FIGS. 4 and 5 show the functioning of the previously mentioned guide helices. The regions 16 and 17 of the drum 3 are respectively provided with guide helices 26 and 27. The cables 5 and 6 care respectively conducted in the guide helices 26 and 27. The guide helices 26 and 27 separate the individual turns of the cables 5 and 6 wound in a spiral (helical) shape around the inner drum 3.2. FIG. 4 shows the case wherein the cables 5 and 6 are partially wound onto the outer drum 3.1, whereby the cable spirals (flights) are broadened in the regions 16 and 17. FIG. 5 shows the case wherein the cables 5, 6 are unwound from the outer drum 3.1, whereby the cable spirals are narrowed in the regions 16, 17. In both cases—which differ in the number and diameter of the turns—the guide helix guarantees a uniform position of the cables 5, 6 in the regions 16, 17. Analogously to the cables 5, 6, the cable 4 is conducted with a guide helix (not depicted) in the region between the outer drum and the inner drum 2.1, 2.2.

The gear train of the apparatus 1 need not necessarily be constructed such that the drums 2 and 3 move in opposite directions. Rather, the train can also be constructed such that the drums 2 and 3 move in the same direction.

The gear train need not necessarily be a toothed gear wheel train, but can also be a chain or belt train.

Instead of the tension spring arrangement, a different energy store can be employed in the embodiment of FIGS. 1 and 2.

Moreover, a different type of drive mechanism can be employed in the embodiment of FIG. 3 instead of the described electromotor 48.

The two drums 2 and 3 need not necessarily have the same diameter, as is the case in the exemplary embodiment. Rather, the diameters of the drums 2 and 3 can differ dependent on the maximum permitted bending radius of the cables being respectively wound on the drums 2 and 3. In this case the gear train should be designed accordingly, so that in winding and unwinding the same length of cable is wound or unwound on each of the drums 2 and 3.

Figure 6:
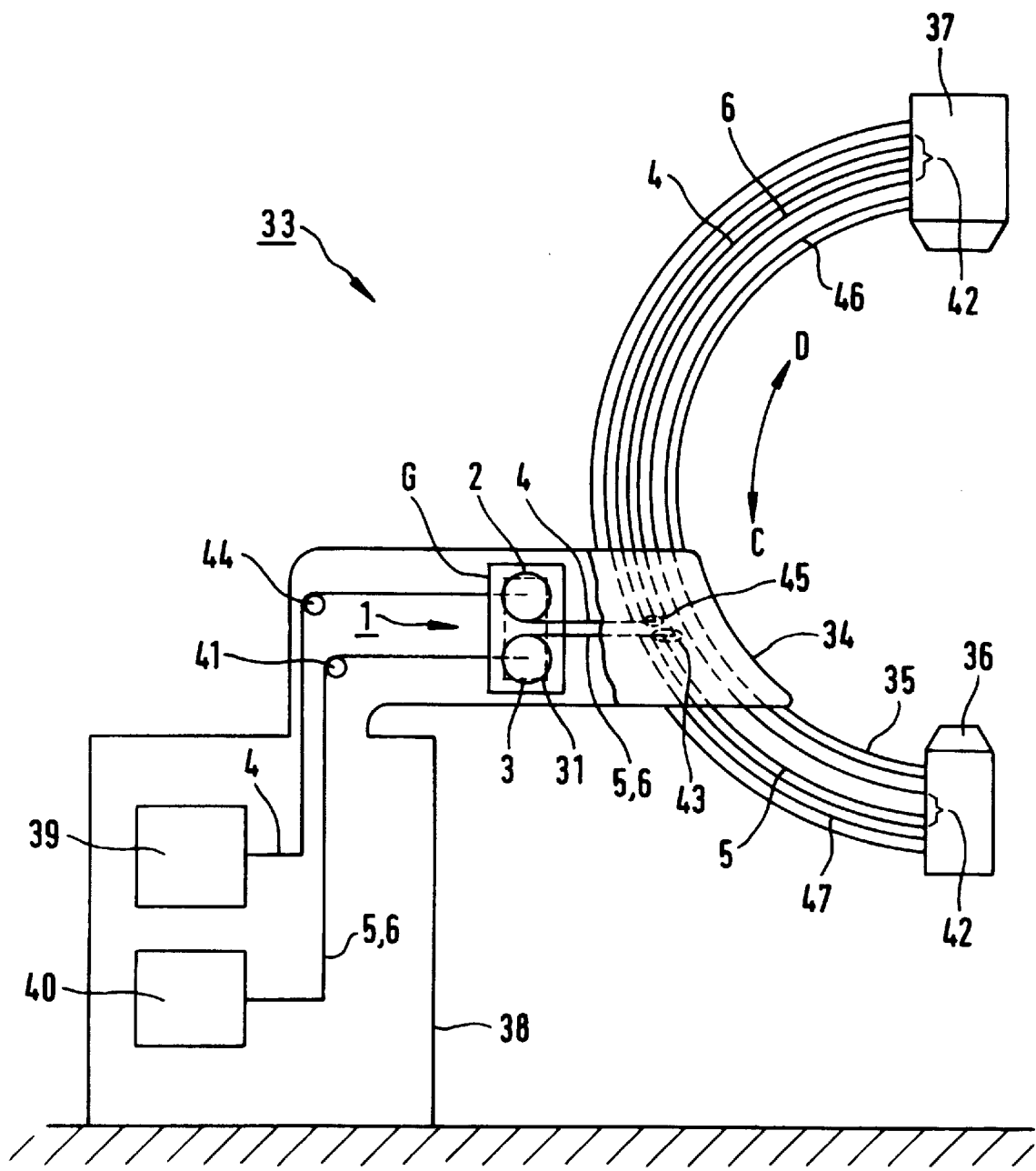
FIG. 6 is a side view of an inventive device, in the form of an x-ray diagnostic apparatus, embodying an inventive winding/unwinding apparatus.

FIG. 6 shows an embodiment of an inventive device with the apparatus 1 (FIG. 1) arranged in a housing G. The apparatus 1 is only schematically depicted in FIG. 6 with its drums 2, 3 and the mounting plate 31. In the exemplary embodiment, the device is a C-arm x-ray device 33. As in the previously described exemplary embodiment of the apparatus 1, the cables of the apparatus 1 are fashioned in the form of round electrical cables which are provided for the transmission of electrical energy and signals.

The C-arm x-ray device 33 has a first part fashioned as holder 34 and a second part fashioned as C-arm 35. The C-arm 35 is held by the holder 34 so as to be displaceable along its perimeter. At its ends the C-arm carries an x-ray source 36 and an x-ray image intensifier 37 in opposing fashion. The holder 34 is secured at another part of the C-arm x-ray device 33, this part containing an energy supply 39 and a control and signal processing unit 40 for operating the x-ray source 36 and the x-ray image intensifier 37. The control and signal processing unit 40 makes available control signals for driving the x-ray source 36 and the x-ray image intensifier 37, and is also provided for signal processing of image signals obtained by the x-ray image intensifier 37.

The previously described apparatus 1 is accepted in the holder 34. The cables 4 to 6 of the apparatus 1 connect the C-arm 35, the holder 34 and the part 38.

The cables 5 and 6 proceed from the control and signal processing unit 40 to the apparatus 1 via a deflection roller 41. The cables 5 and 6 are conducted into the respective regions 16 and 17 of the drum 3 via a side opening 30 of the inner drum 3.2 (cf. FIG. 1) in the manner previously described, are reeled around the inner drum 3.2 in a helical path in the guide helices 26 and 27 and are wound onto the regions 8 and 9 of the outer drum 3.1 (cf. FIG. 4 and FIG. 5). From the drum 3, the cables 5 and 6 are conducted to the C-arm 35 at which they are secured at a point 43 of a shaft 42 of the C-arm 35. The cable 5 is conducted from the point 43 in the shaft 42 to the x-ray source 36, and the cable 6 is conducted from the point 43 in the shaft 42 to the x-ray image intensifier 37.

Analogously to the cables 5 and 6, the cable 4 is conducted from the energy supply 39 to the apparatus 1 via a deflection roller 44. The cable 4 is conducted into the region between the inner and outer drums 2.2, 2.1 via the side opening 12 of the inner drum 2.1 and the opening of the inner drum 2.1, is reeled around the inner drum 2.2 in a helical path in the guide helix (not depicted), is conducted through the opening of the outer drum 2.1 and is wound around the outer drum 2.1. From the outer drum 2.1 the cable 4 is conducted to the C-arm 35, at which it is fixed at a point 45 of the shaft 42. From the point 45 the cable 4 is conducted in the shaft 42 to the x-ray image intensifier 37. The cables 4 and 6 are conducted in the shaft 42 in separate chambers (not depicted).

In the exemplary embodiment the cables 5 and 6 are provided for the transmission of control signals from the control and signal processing unit 40 to the x-ray source 36 and the x-ray image intensifier 37. The cable 6 also serves for the transmission of image signals obtained by the x-ray image intensifier 37 to the control and signal processing unit 40. The cable 4 serves for the transmission of energy from the energy supply 39 that is provided for the x-ray source 36 and the x-ray image intensifier 37. The cable 46 which is conducted in the C-arm 35 from the x-ray image intensifier 37 to the x-ray source 36 therein transmits the energy provided with the cable 4 for the x-ray source 36—which is provided together with the energy for the x-ray image intensifier 37—to the x-ray source 36. A separation of energy cables and signal cables thus ensues by means of the cables 4 to 6 in order to avoid disturbing influences due to crosstalk between energy and signal cables in the operation of the C-arm x-ray device 33.

If the C-arm 35 in the holder 34 is moved in a direction C, then a tensile force is exerted on the cables 4 to 6, so that the cables 4 to 6 are simultaneously unwound from the outer drums 2.1, 3.1. The cables 4 to 6 fixed at the C-arm 35 at the points 43 and 45 lie in a channel 47 of the C-arm 35 which is provided for accepting the cables 4 to 6, this channel 47 being divided into individual chambers (not depicted) for the cables 4 to 6. The unwinding of the cables 4 to 6 from the outer drums 2.1, 3.1 of the apparatus 1 effects a tensioning of the tension spring 22 via the gear train of the apparatus 1. If the C-arm 35 is subsequently moved in a direction D, then the force stored in the tension spring 22 effects winding of the cables 4 to 6 onto the outer drums 2.1, 3.1 of the apparatus 1. If the C-arm 35 is moved in the direction D beyond the starting position of the C-arm 35 depicted in FIG. 6, a tensile force is again exerted on the cables 4 to 6, so that the cables are unwound again from the outer drums 2.1, 3.1. The cables 4 to 6 which are fixed at the points 43, 45 of the C-arm 35 lie in the individual chambers of the channel 47 of the C-arm 35 in the manner previously described. By rotation of the outer drums 2.1, 3.1 and by means of the gear train, the tension spring 22 again stressed, so that in the resetting or return motion of the C-arm 35 in the direction C the cables 4 to 6 can be wound onto the outer drums 2.1, 3. 1 again.

In addition, the holder 34 need not necessarily be connected securely to the part 38 of the device. Rather, the holder 34 can be mounted in pivoting, height-adjustable fashion relative to the part 38. However, in this case at least one other apparatus should be provided in the holder 34 or in the part 38 which conducts the cables 4 to 6 to accommodate the height adjustment and pivoting of the holder 34.

In the case of the C-arm x-ray device 33 the apparatus 1 need not necessarily be provided at the holder 34, but can be allocated to the C-arm 35 in a modified embodiment of the inventive device.

Instead of the apparatus 1 according to FIG. 1, the C-arm x-ray device 33 can also be provided with the apparatus 1 according to FIG. 3.

The device embodying the inventive apparatus 1 need not necessarily be a C-arm x-ray device 33, but can be some other device.

Although modifications and changes may be suggested by those skilled in the art, it is the intention of the inventor to embody within the patent warranted hereon all changes and modifications as reasonably and properly come within the scope of his contribution to the art.

We claim as our invention:

1. An apparatus for winding and unwinding cables comprising:

a first rotatable drum and at least one first cable entrained around said first drum, said first cable, in a first drum winding operation, being wound onto or unwound from said first drum dependent on a direction of rotation of said first drum;

a second rotatable drum and at least one second cable entrained around said second drum, said second drum being disposed non-coaxially relative to said first drum, and said second cable, in a second drum winding operation, either being wound onto or unwound from said second drum dependent on a direction of rotation of said second drum;

a coupling linkage always mechanically connecting said first drum and said second drum for always simultaneously rotating said first drum and said second drum, said coupling linkage causing(g said first drum and said second drum, when rotated, to always simultaneously rotate; and means cooperating with said coupling linkage for operating said coupling linkage to rotate said first drum and said second drum to simultaneously execute said first drum winding operation and said second drum winding operation.

2. An apparatus as claimed in claim 1 wherein said coupling linkage comprises a gear train.

3. An apparatus as claimed in claim 1 wherein said means cooperating with said coupling linkage comprises a tension spring stationarily fixed at a first end and having a second end, a rope connected to said second end of said tension spring, and a rope drum engaging said coupling linkage, said rope being wound onto said rope drum as said first drum and said second drum are rotated and thereby tensioning said tension spring, said tension spring subsequently relaxing when rotation of said first drum and said second drum ceases.

4. An apparatus as claimed in claim 1 wherein said means cooperating with said coupling linkage comprises a drive mechanism.

5. An apparatus as claimed in claim 1 wherein said first drum comprises:

a first outer hollow-cylindrical drum and a first inner hollow-cylindrical drum, said first inner hollow-cylindrical drum being stationary and said first outer hollow-cylindrical drum being mounted to rotate around said first inner hollow-cylindrical drum, said first outer hollow-cylindrical drum and said first inner hollow-cylindrical drum having a space therebetween; and said first cable being wound onto and unwound from said first outer hollow-cylindrical drum and said first outer hollow-cylindrical drum having an opening therein through which said first cable is conducted and is wound around said first inner hollow-cylindrical drum in a helical path, and wherein said second rotatable drum comprises a second outer hollow-cylindrical drum and a second inner hollow-cylindrical drum, said second inner hollow-cylindrical drum being stationary and said second outer hollow-cylindrical drum being mounted to rotate around said second inner hollow-cylindrical drum, said second outer hollow-cylindrical drum and said second inner hollow-cylindrical drum having a space therebetween.

6. An apparatus as claimed in claim 5 wherein said first rotatable drum further comprises a first helical guide disposed around and laterally movable on said first inner hollow-cylindrical drum, and wherein said second rotatable drum further comprises a second helical guide disposed around and laterally movable on said second inner hollow-cylindrical drum.

7. An apparatus as claimed in claim 1 further comprising a first part and a second part, said first part being stationary and said second part being movable relative to said first part, and said second part engaging said first and second cables for movement relative to said first part upon rotation of said first drum and said second drum.

8. An apparatus as claimed in claim 7 further comprising a first electrical component and a second electrical component carried on said second part.

9. An apparatus as claimed in claim 8 wherein said first cable and said second cable, in combination comprise means for transmitting at least one of electrical energy and electrical signals to said first electrical component and to said second electrical component.

10. An apparatus as claimed in claim 8 wherein said first cable comprises means for transmitting said electrical energy and wherein said second cable comprises means for transmitting said electrical signals.

11. An apparatus as claimed in claim 7 wherein said second part comprises a C-arm and wherein said first part comprises a holder for said C-arm, said C-arm having a periphery which moves through said holder, and wherein said first electrical component comprises an x-ray source mounted at a first end of said C-arm and wherein said second electrical component comprises an x-ray receiver mounted at a second end of said C-arm, opposite said x-ray source.

12. An apparatus as claimed in claim 11 wherein said C-arm has a hollow interior, and wherein said first cable and said second cable are fixed to said C-arm in said interior and are conducted through said interior of said C-arm to said x-ray source and to said x-ray receiver, respectively.

\* \* \* \* \*